United States Patent
Song et al.

(10) Patent No.: US 12,139,466 B2
(45) Date of Patent: Nov. 12, 2024

(54) SYNTHESIS OF SUBSTITUTED FURANS

(71) Applicant: BP Corporation North America Inc., Houston, TX (US)

(72) Inventors: Liang Song, San Diego, CA (US); Christopher Phillips, San Diego, CA (US); Lu Yang, San Diego, CA (US); Joseph Binder, Haverford, PA (US); Erin Imsand, San Diego, CA (US)

(73) Assignee: BP Corporation North America Inc., Houston, TX (US)

( * ) Notice: Subject to any disclaimer, the term of this patent is extended or adjusted under 35 U.S.C. 154(b) by 121 days.

(21) Appl. No.: 18/155,340

(22) Filed: Jan. 17, 2023

(65) Prior Publication Data
US 2023/0150962 A1 May 18, 2023

Related U.S. Application Data

(62) Division of application No. 17/613,899, filed as application No. PCT/US2020/042836 on Jul. 20, 2020, now Pat. No. 11,584,730.

(60) Provisional application No. 62/876,301, filed on Jul. 19, 2019.

(51) Int. Cl.
*C07D 307/68* (2006.01)
*C08G 6/00* (2006.01)

(52) U.S. Cl.
CPC .............. *C07D 307/68* (2013.01); *C08G 6/00* (2013.01)

(58) Field of Classification Search
CPC .................................................... C07D 307/68
See application file for complete search history.

(56) References Cited

U.S. PATENT DOCUMENTS

| | | |
|---|---|---|
| 9,260,403 B2 | 2/2016 | Yoshikuni et al. |
| 2017/0050944 A1 | 2/2017 | Kambourakis et al. |
| 2018/0057897 A1 | 3/2018 | Binder et al. |
| 2022/0144791 A1 | 5/2022 | Song et al. |

FOREIGN PATENT DOCUMENTS

WO 2005/003374 A1 1/2005

OTHER PUBLICATIONS

International Search Report and Written Opinion for International Application No. PCT/US2020/042836, dated Feb. 10, 2021.
Cheng et al., 1985 "Differentially Protected Ribofuranoid Glycals" Journal of Organic Chemistry, vol. 50, pp. 2778-2780.

*Primary Examiner* — Golam M Shameem
(74) *Attorney, Agent, or Firm* — Biospark Intellectual Property Law

(57) ABSTRACT

A method is provided of preparing a compound of formula II:

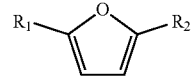

Formula II where: $R_1$ and $R_2$ are independently selected from —$CH_2OR'$, —CHO, —COOR' and —H,
provided that $R_1$ and $R_2$ are not both —H; and
R' is selected from —H and $C_{1-6}$ hydrocarbyl groups, from a compound of formula I:

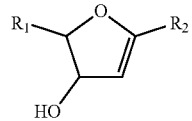

Formula I the compounds of formulas I and II being optionally in the form of a salt. The method comprises dehydrating the compound of formula I at: a pH in the range of from 0 to 6 or 8 to 11.5; and a temperature in the range of from 10 to 80° C. The method is particularly useful for synthesizing substituted furans from compounds derived from sugars.

21 Claims, 2 Drawing Sheets

SYNTHESIS OF SUBSTITUTED FURANS

This application is a divisional of U.S. application Ser. No. 17/613,899, which is a § 371 application of PCT application no. PCT/US2020/042836, filed Jul. 20, 2020, the contents of which are incorporated herein in their entireties by reference thereto. PCT application no. PCT/US2020/042836 claims the priority benefit of U.S. provisional application No. 62/876,301, filed Jul. 19, 2019.

The present disclosure relates to methods for synthesizing substituted furans, in particular to methods for synthesizing furans from compounds derived from sugars.

BACKGROUND OF THE DISCLOSURE

Substituted furans are a class of compounds of significant interest, since they can be derived from renewable resources such as sugars and are useful in a wide range of applications. Substituted furans are useful in the preparation of polymers. 2,5-Furandicarboxylic acid (FDCA) is particularly useful, as it represents a renewable monomer which can be used in polymers instead of terephthalic acid. Moreover, polymers such as polyethylene 2,5-furandicarboxylate (PEF) which contain FDCA can exhibit improved properties as compared to the equivalent terephthalate-containing polymer.

However, producing substituted furans such as FDCA from renewable sources has been challenging. In particular, many of the steps involved in converting sugars to substituted furans exhibit low selectivity and therefore low yield. Moreover, some methods require the use of fructose as a starting material, rather than more readily obtainable sugars such as glucose. Though some methods use glucose, it is often processed into fructose, which can be inefficient.

Recently, there have been a number of advances in the production of substituted furans. For example, a method is disclosed in US 2017/050944 in which gluconic acid derivatives are chemically dehydrated in the presence of a dehydration catalyst to give FDCA. A further method is disclosed in US 2018/057897 in which 5-hydroxymethyl furoic acid, a substituted furan, is prepared from 2-keto-3-deoxy-gluconate (KDG).

Though the recent developments are promising, the relatively high temperatures and high acid concentration required lead to relatively modest yields with significant quantities of byproduct. Such methods can furthermore only deliver higher yields when the dehydration is performed in a solvent system which is not fully aqueous, e.g. in an acetic acid- or ethanol-based system, which increases the economic cost of the process. Where predominantly aqueous systems have been used, a low yield is obtained.

Accordingly, there is a need for further methods for preparing substituted furans which preferably address one or more of the drawbacks associated with existing preparation methods.

SUMMARY OF THE DISCLOSURE

The present disclosure provides a method of preparing a compound of formula II:

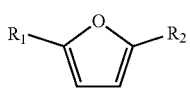

Formula II where: $R_1$ and $R_2$ are independently selected from —$CH_2OR'$, —CHO, —COOR' and —H,
provided that $R_1$ and $R_2$ are not both —H; and
R' is selected from —H and $C_{1-6}$ hydrocarbyl groups, from a compound of formula I:

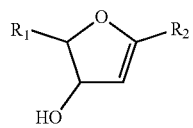

Formula I the compounds of formulas I and II being optionally in the form of a salt. The method comprises dehydrating the compound of formula I at a pH in the range of from 0 to 6 or 8 to 11.5; and a temperature in the range of from 10 to 80° C.

It has surprisingly been found that compounds of formula I represent useful materials for preparing substituted furans. In particular, they may be used in methods in which relatively mild conditions are employed, yet which may deliver high levels of conversion and selectivity for substituted furans of formula II in a short space of time.

Also provided is a method of preparing a compound of formula III:

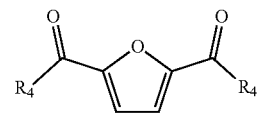

Formula III where: $R_4$ is selected from —OH and —R';
the compound of formula III being optionally in the form of a salt. The method comprises preparing a compound of formula II using a method as defined herein; and, provided that the compounds of formula II and III do not have the same structure, converting the compound of formula II into a compound of formula III.

The present disclosure further provides a method of preparing a polymer comprising a polymeric unit of formula IV:

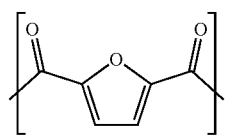

Formula IV

The method comprises preparing a compound of formula III or a salt thereof using a method as defined herein; and forming the polymer by carrying out a polymerisation reaction using the compound of formula III.

Also provided is a compound of formula I:

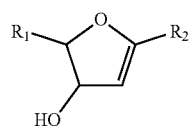

Formula I where: $R_1$ and $R_2$ are independently selected from —$CH_2OR'$, —CHO, —COOR' and —H, provided that $R_1$ and $R_2$ are not both —H; and R' is selected from —H and $C_{1-6}$ hydrocarbyl groups, the compound of formula I being optionally in the form of a salt.

DETAILED DESCRIPTION

Figure 1:
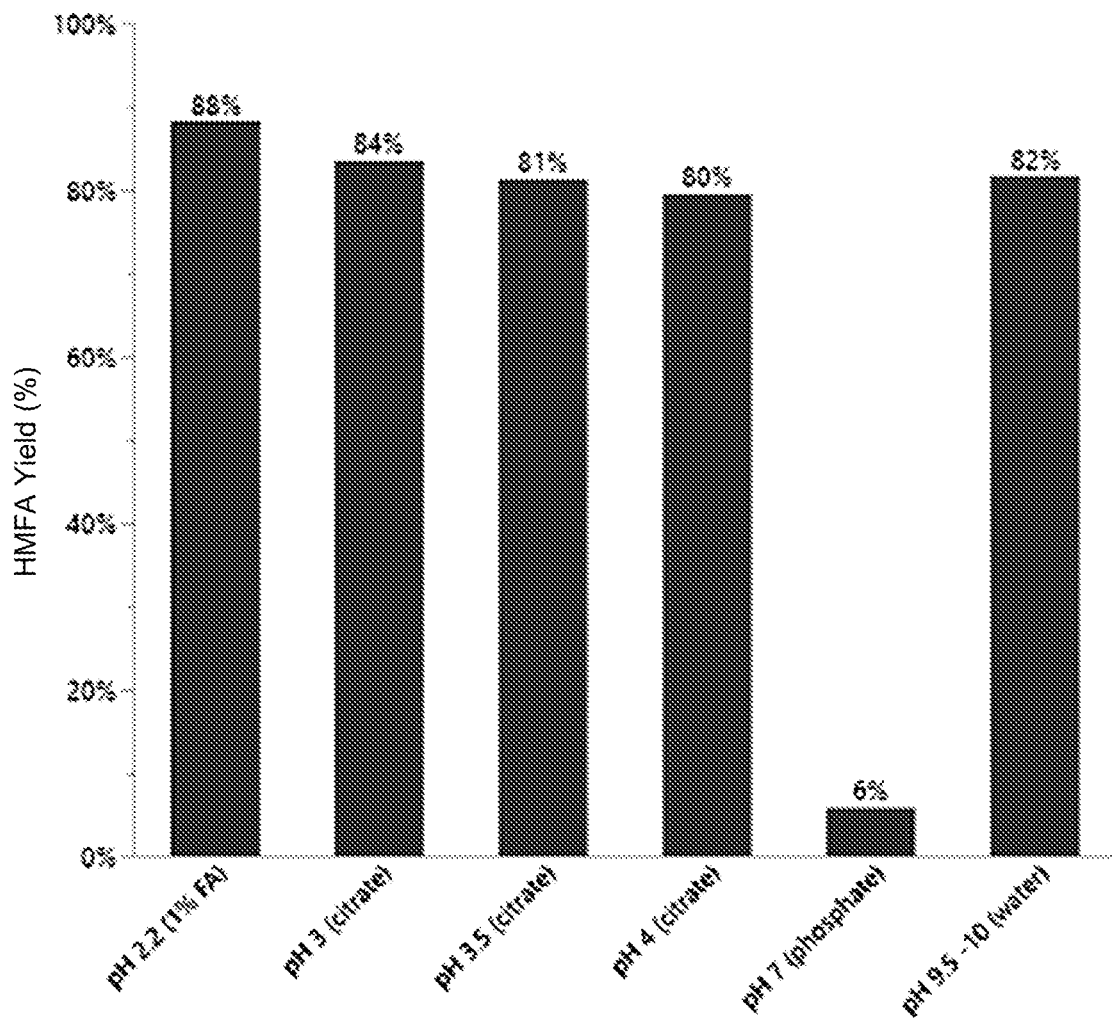
FIG. 1 is a graph showing the yield obtained when a compound of formula I is dehydrated to form a compound of formula II under mild conditions but at varying pH levels.

The present disclosure provides a method of preparing a compound of formula II from a compound of formula I. Thus, the method involves performing the following dehydration reaction:

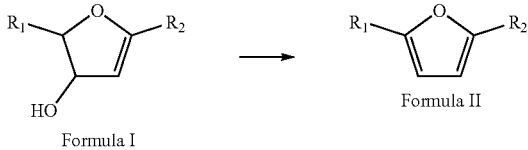

It will be appreciated that a molecule of water is lost from each molecule of the compound of formula I as it converts to a compound of formula II.

Dehydration Reaction Conditions

The method of the present disclosure involves dehydrating the compound of formula I under relatively mild conditions. Specifically, the dehydration reaction is carried out at a pH in the range of from 0 to 6 or 8 to 11.5, and a temperature in the range of from 10 to 80° C.

The dehydration reaction may be carried out at a temperature of up to 70° C., preferably up to 55° C., and more preferably up to 50° C. The dehydration reaction may be carried out at a temperature of at least 15° C., preferably at least 20° C., and more preferably at least 25° C. Thus, the dehydration reaction may be carried out a temperature of from 15 to 70° C., preferably from 20 to 55° C., and more preferably from 25 to 50° C.

In some instances, the dehydration reaction is carried out under acidic conditions. For instance, the dehydration reaction may be carried out at a pH of up to 5, preferably up to 4, and more preferably up to 3.5. The dehydration reaction may be carried out at a pH of at least 1.5, preferably at least 1.75, and more preferably at least 2. Thus, the dehydration reaction may be carried out at a pH of from 1.5 to 5, preferably from 1.75 to 4, and more preferably from 2 to 3.5.

In other instances, the dehydration reaction is carried out under basic conditions. For instance, the dehydration reaction may be carried out at a pH of at least 8.5, preferably at least 9, and more preferably at least 9.5. The dehydration reaction may be carried out at a pH of up to 11.5, preferably up to 11, and more preferably up to 10.5. Thus, the dehydration reaction may be carried out at a pH of from 8.5 to 11.5, preferably from 9 to 11, and more preferably from 9.5 to 10.5.

pH may be measured using conventional methods, e.g. using a pH probe, under the conditions of the reaction.

A suitable pH may be imparted on the reaction mixture by virtue of the $R_1$ and $R_2$ groups in the compound of formula I, for instance if $R_1$ and/or $R_2$ are acidic groups such as —COOH or basic groups such as —COO$^-$ where the compound of formula I is present in the form of a salt.

However, at least one of an acid, base or buffer will typically be added to the reaction mixture to adjust the pH. A buffer will generally be used, optionally with an additional acid or base.

The acid and base will typically catalyse the reaction, i.e. they will not be consumed during the course of the reaction.

A wide range of acids may be used. For instance, the acid may be selected from organic acids, such as from $C_{1-6}$ carboxylic acids. The acid may be selected from inorganic acids, such as from hydrochloric acid, sulfuric acid, phosphoric acid, nitric acid and hydrobromic acid.

In some embodiments, an acid may be used in the form of a solid. Thus, the reaction may be carried out using a heterogeneous, and preferably solid-phase, catalyst.

A wide range of bases may be used. For instance, the base may be selected from nitrogen-containing bases such as ammonia, an amine (e.g. a primary, secondary or tertiary, and preferably tertiary amine) and nitrogen-containing heterocycles (e.g. pyridine, imidazole, piperidine or piperazine). The base may be selected from metal-containing bases such as metal hydroxides (e.g. alkali or alkaline earth metal hydroxides), metal oxides (e.g. transition metal oxides) or metal carbonates (e.g. alkali or alkaline earth metal carbonates or hydrogencarbonates).

As with the acid, in some embodiments, a base may be used in the form of a solid.

A wide range of buffers may be used. For instance, the buffer may be selected from a citrate buffer, a formate buffer, an acetate buffer, a carbonate buffer, a phosphate buffer, an N-cyclohexyl-2-aminoethanesulfonic acid (CHES) buffer, a borate buffer, a citrate-phosphate buffer, a 2-[4-(2-hydroxyethyl)piperazin-1-yl]ethanesulfonic acid (HEPES) buffer, a tris(hydroxymethyl)-aminomethane (Tris) buffer, a 2-(N-morpholino)ethanesulfonic acid (MES) buffer, a sugar acid buffer, or an ammonia buffer.

The pH will typically remain fairly constant during the reaction, particularly where a buffer is used. However, it may be desirable to monitor and, where necessary, adjust the pH (e.g. so that it remains with a range of ±0.8, and preferably ±0.5 of the target pH) during the course of the dehydration reaction, for instance where the reaction is carried out in a continuous mode.

The dehydration reaction may be carried out in the presence of a protic solvent, such as water. Preferably, the solvent system in which the reaction is carried out contains water in an amount of at least 50%, preferably at least 70%, and more preferably at least 90% by volume. In some instances, the solvent system consists substantially of water.

The compound of formula I may be added to the reactor in an amount of greater than 5 g/L, preferably greater than 10 g/L, and more preferably greater than 20 g/L of solvent. However, in some embodiments, e.g. where a one-pot synthesis is carried out in which the compound of formula I is prepared from a sugar acid in the same reactor as the compound of formula II (this is described in greater detail below), the concentration of the compound of formula I may be low. In these instances, the compound of formula I may be present in the reactor in an amount of greater than 0.1 g/L, preferably greater than 0.2 g/L, and more preferably greater than 0.5 g/L. Where compounds of formula I are present in the form of a salt, these values represent the amount of the corresponding salt-free form (e.g. if the compound of formula I contains the group —COOLi, then the corresponding salt-free form would contain the group —COOH).

The dehydration reaction will generally be conducted at ambient pressure, i.e. without the application or removal of pressure. Thus, the dehydration reaction may take place at a pressure of about 1 atm, e.g. from 0.95 to 1.05 atm. However, higher pressures may also be used.

The dehydration reaction will usually take place under agitated conditions, e.g. under stirring.

An advantage of the present invention is that the dehydration reaction takes place very quickly and at high yield.

In some instances, the dehydration reaction may be carried out as a batch process. A batch process may be carried out for a period of up to 336 hours, preferably up to 168 hours, more preferably up to 72 hours. Since the dehydration reaction takes place quickly, in some instances, and even on an industrial scale, the batch process may be carried out for a period of up to 24 hours or even less, e.g. for a period of up to 12 hours. Batch processes will be carried out in a batch reactor system.

However, the dehydration reaction will preferably be carried out as a continuous process. A continuous process may be carried out for at least 14 days, preferably at least 30 days, and more preferably at least 60 days. Continuous processes will be carried out in a continuous reactor system.

A further advantage is that minimal byproducts are formed, even where a one-pot synthesis is carried out in which the compound of formula I is prepared from a sugar-acid in the same reactor as the compound of formula II (this is described in greater detail below).

The dehydration reaction is preferably carried out on an industrial scale. Thus, the dehydration reaction may be carried out in a reactor having a volume of greater than 100 L, preferably greater than 500 L, and more preferably greater than 1000 L.

The compound of formula II may be produced in an amount of greater than 5 g/L, preferably greater than 10 g/L, and more preferably greater than 20 g/L of solvent.

The compounds of formula II may be obtained in a yield of at least 60%, preferably at least 80%, preferably at least 90%, preferably at least 95%, preferably at least 99%, and more preferably at least 99.5% yield from formula I.

Compounds

Compounds of formula I and II are shown below:

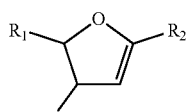

Formula I

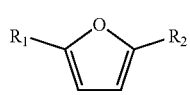

Formula II

It will be appreciated that groups present as $R_1$ and $R_2$ in the compounds of formula I will not be modified during the course of the dehydration reaction, i.e. $R_1$ and $R_2$ are the same in compounds of formula I and formula II.

$R_1$ and $R_2$ are independently selected from —$CH_2OR'$, —CHO, —COOR' and —H. $R_1$ and $R_2$ are not both —H or, in other words, the compounds of formula I and II must be substituted.

R' is selected from H and $C_{1-6}$ hydrocarbyl groups. Preferably, R' is selected from —H and $C_{1-4}$ hydrocarbyl groups, more preferably from —H and $C_{2-3}$ hydrocarbyl groups, and most preferably is —H. The hydrocarbyl group is preferably an alkyl group, though other groups such as alkenyl groups may be present.

$R_1$ and $R_2$ are preferably selected from —$CH_2OH$, —CHO, —COOH and —H, and more preferably from —$CH_2OH$, —CHO, —COOH.

At least one of $R_1$ and $R_2$ may be selected from —COOH.

At least one of $R_1$ and $R_2$ may be selected from —$CH_2OH$.

Preferably, one of $R_1$ and $R_2$ is selected from —$CH_2OH$ and the other is selected from —COOH, and more preferably $R_1$ is —$CH_2OH$ and $R_2$ is —COOH. Thus, the compound of formula I preferably has the structure:

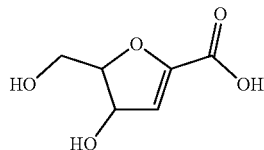 [SMILES: O=C(O)C1=CC(O)C(CO)O1]

This structure is particularly preferred, since it is derived from 2-keto-3-deoxygluconate which, in turn, may be derived from glucose. This preferred structure gives a compound of formula II which is 5-hydroxymethyl-2-furoic acid:

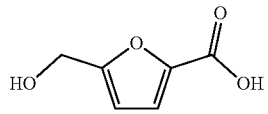

In other embodiments, both $R_1$ and $R_2$ are selected from —COOH. These embodiments advantageously allow the compound of formula II to be used directly in a polymerization reaction.

The compounds of formula I and II may be in the form of a salt. Preferred salts may be selected from alkali metal salts (e.g. lithium, sodium or potassium salts) and alkaline earth metal salts (e.g. magnesium or calcium salts). Carboxyl (—COOH) groups are particularly suitable for forming salts. A compound of formula II may be in the same salt form as the compound of formula I.

Preparing Compounds of Formula I

The compounds of formula I may be prepared from a precursor compound having the following formula:

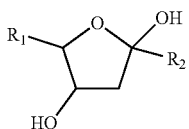

Precursor I

It will be appreciated that precursor I may convert between other tautomeric forms in the reaction mixture, e.g.

it may be present in the form of a straight-chain molecule or in the form of a 5- or 6-membered ring. 5- or 6-membered ring forms may include, in addition to the form shown above, 5- or 6-membered lactones where one of $R_1$ or $R_2$ is a COOH group, and 6-membered pyranose compounds where one of $R_1$ or $R_2$ represents $CH_2OH$ group.

Thus, the method of the present disclosure may comprise providing the compound of formula I from precursor I, e.g. by a dehydration reaction:

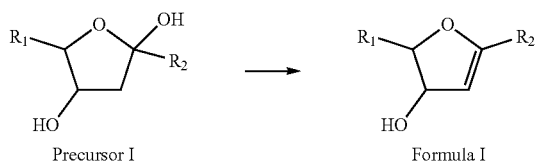

Precursor I    Formula I

The dehydration reaction is preferably carried out in the presence of an enzyme, such as a dehydratase.

The compound of formula II may be obtained in a yield of at least 50%, preferably at least 70%, and preferably at least 90% from precursor I.

In some embodiments, a precursor I may be converted into a compound of formula I and, in the same reactor, the compound of formula I converted into a compound of formula II. Thus, the reactions may advantageously be carried as a one-pot synthesis, i.e. a synthesis in which an intermediate work-up is not involved.

Where a one-pot synthesis is carried out, though an enzyme may be present to promote the conversion of the precursor I to a compound of formula I, the enzyme will typically not be capable of converting the compound of formula I into a compound of formula II under the reaction conditions of the present disclosure. In these embodiments, it is desirable to use a pH level which promotes the conversion of a compound of formula I to a compound of formula II, but which does not reduce the activity of the enzyme which is, in the same pot, promoting the conversion of precursor I to a compound of formula I. As mentioned above, in such embodiments, preferred acidic pH levels are from 1.5 to 6, preferably from 2 to 6, and more preferably from 3.5 to 6. Preferred basic pH levels are from 8 to 11.5, preferably from 8 to 10.5, and more preferably from 8 to 9.5.

In other embodiments, the method of the present disclosure may comprise converting a precursor I into a compound of formula I, isolating the compound of formula I, and subsequently converting a compound of formula I into a compound of formula II.

Preferably, compounds of formula I are obtained from sugar acids. Sugar acids are well-known in the art as monosaccharides which comprise at least one carboxyl (—COOH) group. Thus, compounds of formula I may be obtained from a precursor I in which at least one of $R_1$ and $R_2$, and preferably $R_2$, is —COOH.

The method of the present disclosure may further comprise providing the sugar acid from an acid-free sugar. It will be appreciated that, in the context of the present disclosure, the term acid-free sugar is intended to denote monosaccharides which do not contain a —COOH group. In particular, the acid sugar may be derived from glucose, e.g. according to the following route:

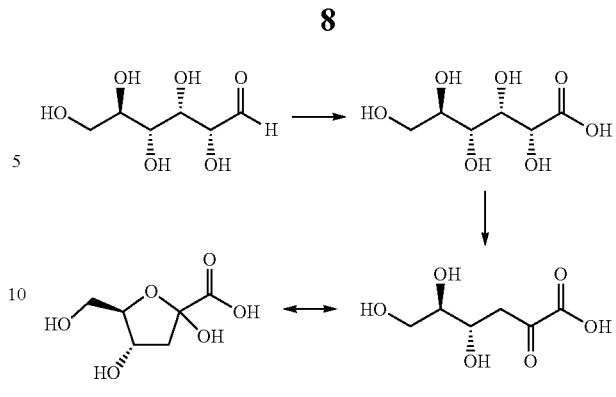

The above route shows oxidation of glucose, followed by dehydration. Alternatively, glucose may be dehydrated and then oxidised, although this is less preferred. Similarly, although the above route shows the preferred stereochemistry for glucose, any other stereochemistry may be present.

The conversion of glucose into an acid sugar is preferably carried out enzymatically, for instance with a first enzyme for the oxidation step and a second enzyme for the dehydration step. Suitable methods for converting glucose into 2-keto-3-deoxygluconate are described in US 2018/057897, the contents of which is hereby incorporated by reference.

Alternatively, compounds of formula I may be prepared synthetically. The skilled person would be able to determine suitable methods.

Using Compounds of Formula II

Compounds of formula II may be used in a method of preparing a compound of formula III:

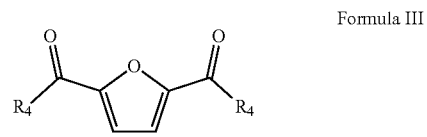

Formula III

Thus, according to a further aspect, the present disclosure provides a method of preparing a compound of formula III. The method comprises preparing a compound of formula II using a method as defined herein, and, provided that the compounds of formula II and III do not have the same structure, converting the compound of formula II into a compound of formula III.

Thus, the method comprises carrying out the following reaction:

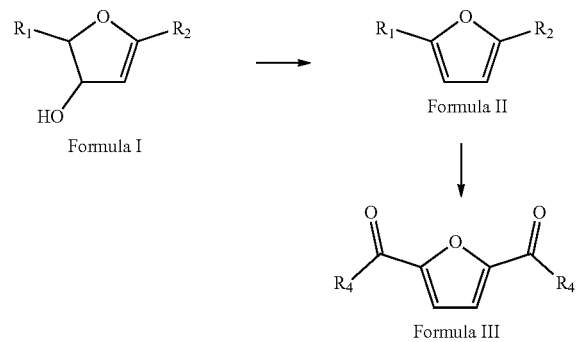

$R_1$ and $R_2$ are as described above.

$R_4$ is selected from —OH and —R', where R' is as described above. Preferably, $R_4$ is OH.

The compound of formula III may be in the form of a salt. Preferred salts may be selected from alkali metal salts (e.g. lithium, sodium or potassium salts) and alkaline earth metal salts (e.g. magnesium or calcium salts). Carboxyl (—COOH) groups are particularly suitable for forming salts. A compound of formula III may be in the same salt form as the compound of formula II.

In preferred embodiments, at least one of $R_1$ and $R_2$ in formula II is selected from —$CH_2OH$ and —COR', and the method comprises oxidising the compound of formula II so as to convert the at least one —$CH_2OH$ and —COR' group into —$COR_4$, where $R_4$ is OH. Suitable oxidation conditions are known in the art.

In some embodiments, a compound of formula I may be converted into a compound of formula II and, in the same reactor, a compound of formula II converted into a compound of formula III. Thus, the reactions may advantageously be carried as a one-pot synthesis, i.e. a synthesis in which an intermediate work-up is not involved.

In alternative embodiments, a compound of formula I may be converted into a compound of formula II in a first reactor, and then the compound of formula II converted into a compound formula III in a second reactor. In these embodiments, the compound of formula II may be extracted and/or purified before it is transferred to the second reactor.

Compounds of formula III represent useful monomers in the preparation of polymers. Thus, in another aspect of the present disclosure, a method is provided of preparing a polymer comprising a polymeric unit of formula IV:

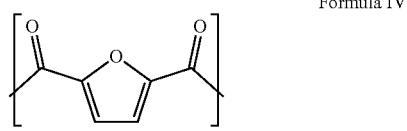

Formula IV

The method comprises preparing a compound of formula III, or a salt thereof, using a method as defined herein, and forming the polymer by carrying out a polymerisation reaction using the compound of formula III.

Typically, the compound of formula III will be isolated, and optionally purified, before it is used to prepare a polymeric unit of formula IV.

The present disclosure further provides compounds of formula II, compounds of formula III or polymers comprising a polymeric unit of formula IV which are obtainable using the methods described herein.

The disclosure will now be described with reference to the accompanying non-limiting examples.

EXAMPLES

Example 1: Dehydration of a Compound of Formula I at Various pH Levels

Experiments were conducted to determine whether compounds of formula I could be dehydrated to compounds of formula II with a high yield under mild conditions. The following compound of formula I was used:

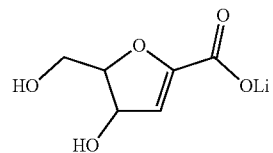

A 1 mM aqueous solution of the compound of formula I was diluted 20-fold by volume using buffer, water, or 1% formic acid. Aqueous citric acid solutions (50 mM) were prepared and adjusted with sodium hydroxide to give citrate acid buffers with pH levels of 3, 3.5 and 4. A sodium phosphate buffer (50 mM) was used to give a pH of 7. Water was used to give a pH of ~9.5-10.1% formic acid was used to give a pH of 2.2. Each reaction mixture was incubated in a 55° C. oven for 18 hours. A sample of each reaction mixture after said 18 hours of incubation was analysed by LC-MS/MS to determine the concentration of the compound of formula II, i.e. 5-hydroxymethyl-2-furoic acid (HMFA). FIG. 1 shows the yield obtained in each reaction.

It can be seen that a very high yield of the compound of formula II was obtained under acid or basic conditions, whereas a low yield was obtained at or around neutral pH. Thus, this example demonstrates a viable method of producing the compound of formula II under relatively mild conditions.

Example 2: Dehydration Yield of a Compound of Formula I with Time

Experiments were conducted to determine whether dehydration of a compound of formula I under mild conditions takes place quickly enough to be industrially viable. The compound of formula I that was used in Example 1 was also used in these experiments, thereby giving HMFA as the compound of Formula II.

Figure 2:
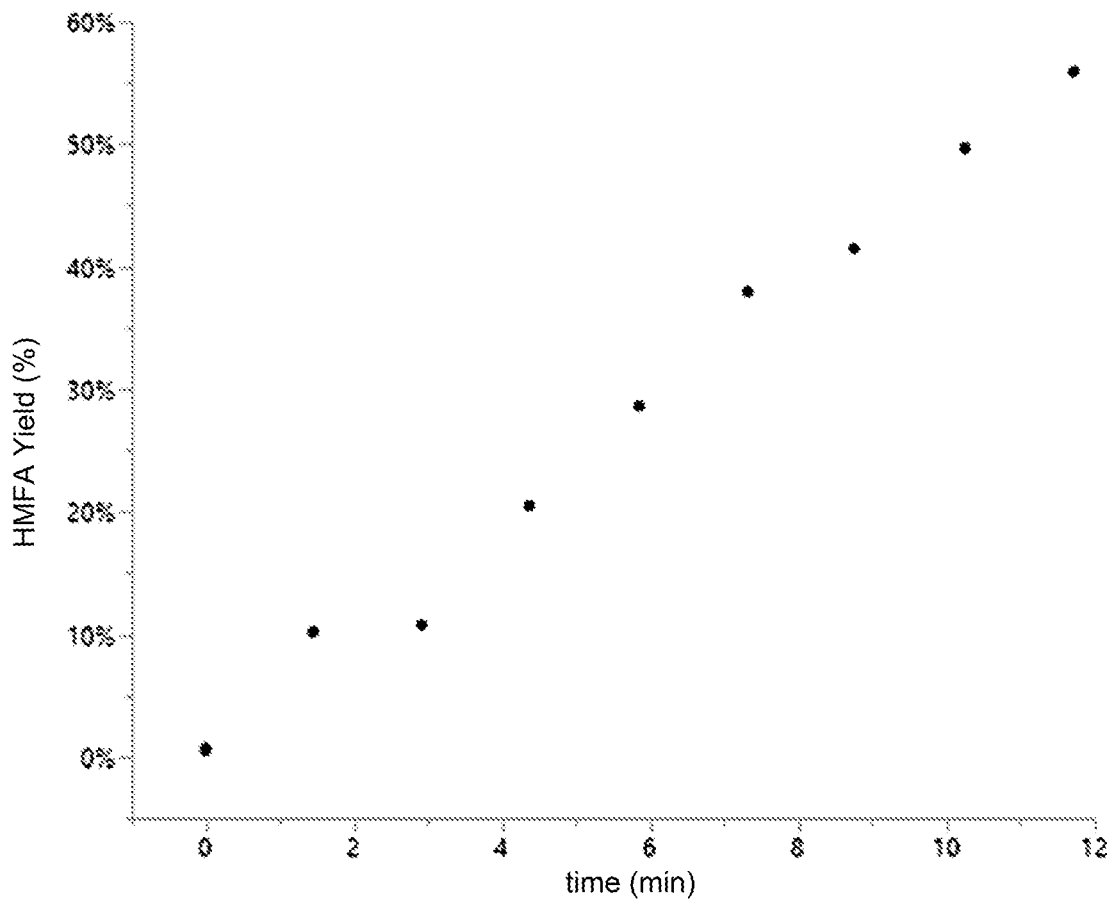
FIG. 2 is a graph showing the yield obtained at different time points during the conversion of a compound of formula I into a compound of formula II under mild conditions.

A 10 mM solution of the compound of formula I was diluted with a citrate buffer (50 mM) to give a 2.5 mM solution of the compound of formula I having a pH of 3.5. The resulting reaction mixture was incubated at 35° C. A sample was taken roughly every 1.5 minutes and analysed by LC-MS/MS. The results are shown in FIG. 2.

It can be seen that the compound of formula I dehydrates extremely quickly under mild conditions, with approximately 50% conversion observed in just 10 minutes.

Example 3: Dehydration of Other Compounds of Formula I Under Mild Conditions

Experiments were conducted to determine whether other compounds of formula I could be dehydrated under mild conditions. The following compounds were used in the experiments:

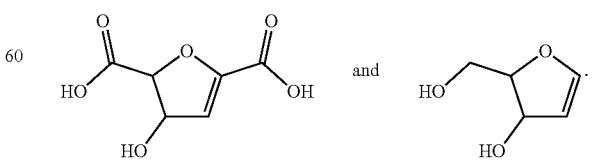

Both compounds converted to the corresponding compounds of formula II under mild conditions. A temperature as low as 18° C. was even used to quantitatively convert the second compound (i.e. in which $R_1$ is —$CH_2OH$ and $R_2$ is H).

Comparative Example: Dehydration of 2-keto-3-deoxygluconate Under Mild Conditions Experiments were conducted to determine whether 2-keto-3-deoxygluconate (KDG) could be dehydrated under mild conditions to give HMFA, i.e. a compound of formula II, in a good yield.

Figure 3:
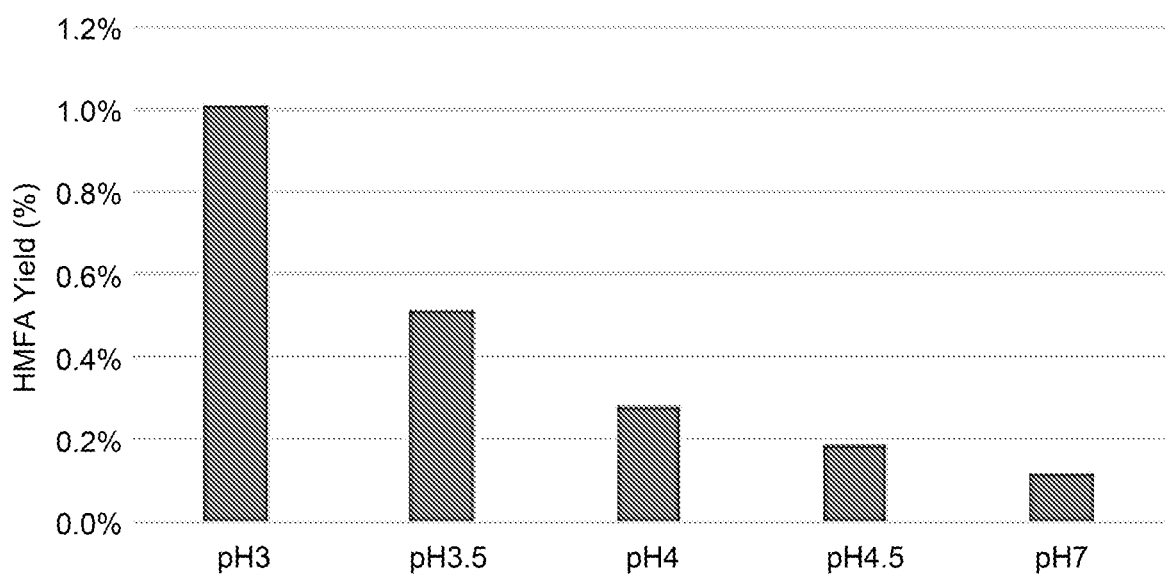
FIG. 3 is a graph showing the yield obtained when 2-keto-3-deoxygluconate, which is not a compound of formula I, is dehydrated under mild conditions but at varying pH levels to give a compound of formula II.

McIlvaine's buffer was prepared using a combination of 200 mM disodium hydrogen phosphate and 100 mM citric acid for use in reaction mixtures having a pH of 3, 3.5, 4, or 4.5. 100 mM sodium phosphate buffer was prepared to serve as a neutral pH control. 1 mL of 2 mM KDG in its sodium salt form was combined with 1 mL of buffer and incubated at 55° C. in an oven for 27 hours. A sample from each reaction was analysed by LC-MS/MS to determine the concentration of HMFA. The results are shown in FIG. 3.

Unlike compounds of formula I, the yield observed on dehydrating KDG to HMFA under mild conditions was no more than 1%, even after 27 hours.

The invention claimed is:
1. A method of preparing a compound of formula III:

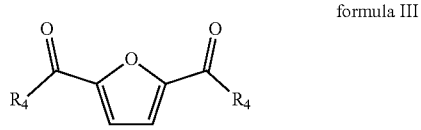

formula III wherein:
$R_4$ is selected from —OH and R'; and
R' is selected from —H and —$C_{1-6}$ hydrocarbyl groups;
the method comprising:
(a) preparing a compound of formula II:

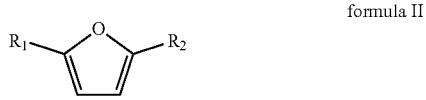

formula II wherein:
$R_1$ and $R_2$ are independently selected from —$CH_2OR'$, —CHO, —COOR' and
—H, provided that $R_1$ and $R_2$ are not both —H;
from a compound of formula I:

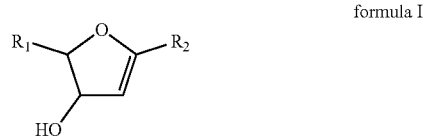

formula I by dehydrating the compound of formula I under acidic or basic pH conditions at:
a pH in the range of from 0 to 6 or 8 to 11.5; and
a temperature in the range of from 10 to 80° C.; and
(b) converting the compound of formula II into a compound of formula III;

the compounds of formula I, II, and III being optionally in the form of a salt; and provided that the compounds of formula II and III do not have the same structure.

2. The method of claim 1, wherein $R_4$ is selected from —H and —OH.

3. The method of claim 1, wherein at least one of $R_1$ and $R_2$ is —$CH_2OH$, and the method comprises oxidizing the compound of formula II to the compound of formula III.

4. The method of claim 1, wherein $R_1$ and $R_2$ are independently selected from —$CH_2OH$, —CHO, —COOH and —H.

5. The method of claim 1, wherein at least one of $R_1$ and $R_2$ is selected from —COOH and —$CH_2OH$.

6. The method of claim 1, wherein both $R_1$ and $R_2$ are —COOH.

7. The method of claim 1, wherein one of $R_1$ and $R_2$ is —$CH_2OH$ and the other is —COOH.

8. The method of claim 1, wherein $R_1$ is —$CH_2OH$ and $R_2$ is —COOH.

9. The method of claim 1, wherein the dehydration reaction is carried out at a temperature in the range of from 15 to 70° C.

10. The method of claim 1, wherein the dehydration reaction is carried out at a pH in the range of from 1.5 to 5.

11. The method of claim 1, wherein the dehydration reaction is carried out at a pH in the range of from 8.5 to 11.5.

12. The method of claim 1, wherein the dehydration reaction is carried out in the presence of a heterogeneous catalyst; and/or a buffer.

13. The method of claim 1, wherein the dehydration reaction is carried out in the presence of a protic solvent.

14. The method of claim 13, wherein the protic solvent is water.

15. The method of claim 1, wherein the dehydration reaction is carried out as a continuous process.

16. The method of claim 1, wherein the dehydration reaction is carried out as a batch process.

17. The method of claim 1, wherein the compounds of formula I, formula II, and formula III are in the form of an alkali metal or alkaline earth metal salt.

18. The method of claim 1, wherein the method comprises providing the compound of formula I from the following precursor I:

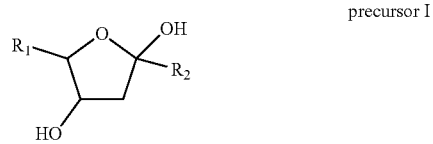

precursor I wherein conversion of precursor I into the compound of formula I is carried out in the presence of an enzyme.

19. The method of claim 18, wherein precursor I is converted into a compound of compound of formula I, and the compound of formula I is converted into a compound of formula II, in the same reactor.

20. The method of claim 1, wherein the method comprises providing the compound of formula I from a sugar acid.

21. The method of claim 1, wherein the dehydration reaction is carried out in the presence of a citrate buffer, a formate buffer, an acetate buffer, a carbonate buffer, a phosphate buffer, an N-cyclohexyl-2-aminoethanesulfonic acid (CHES) buffer, a borate buffer, a citrate-phosphate buffer, a 2-[4-(2-hydroxyethyl)piperazin-1-yl]ethanesulfonic acid (HEPES) buffer, a tris(hydroxymethyl)aminomethane (Tris), 2-(N-morpholino)ethanesulfonic acid (MES) buffer, a sugar acid buffer, or an ammonia buffer.

* * * * *